United States Patent [19]

Gruber et al.

[11] Patent Number: 4,791,080
[45] Date of Patent: Dec. 13, 1988

[54] OXIDATIVE CATALYST REGENERATION

[75] Inventors: Wilheim Gruber, Darmstadt; Klaus Langerbeins, Langen; Wolfgang Ruppert, Seeheim-Jugenheim, all of Fed. Rep. of Germany

[73] Assignee: Röhm GmbH, Darmstadt, Fed. Rep. of Germany

[21] Appl. No.: 78,224

[22] Filed: Jul. 27, 1987

[30] Foreign Application Priority Data

Aug. 2, 1986 [DE] Fed. Rep. of Germany ....... 3626255

[51] Int. Cl.$^4$ .................. B01J 27/28; B01J 38/14; C07C 57/05; C07C 51/377
[52] U.S. Cl. .................................. 502/52; 502/38; 560/214; 562/535; 562/599
[58] Field of Search .................. 502/38, 51, 52, 209; 562/599, 535; 560/214

[56] References Cited

U.S. PATENT DOCUMENTS

| | | | |
|---|---|---|---|
| 4,052,333 | 10/1977 | Lee | 252/416 |
| 4,146,574 | 3/1979 | Onoda et al. | 423/299 |
| 4,370,490 | 8/1981 | Gruber et al. | 560/214 |
| 4,471,061 | 9/1984 | Shaw et al. | 502/34 |

FOREIGN PATENT DOCUMENTS

| | | |
|---|---|---|
| 0046840 | 10/1982 | European Pat. Off. . |
| 0071137 | 9/1983 | European Pat. Off. . |
| 0079491 | 7/1985 | European Pat. Off. . |
| 0113084 | 2/1986 | European Pat. Off. . |
| 2836309 | 2/1979 | Fed. Rep. of Germany ...... 562/599 |
| 3145091 | 5/1983 | Fed. Rep. of Germany ...... 562/599 |
| 2116003 | 7/1972 | France . |
| 163755 | 12/1981 | Japan ..................................... 502/38 |

OTHER PUBLICATIONS

Ullmanns Encyclopaedie der technishen Chemie, 4th Edition, vol. 13, 518, 544–549, 558–565.

Primary Examiner—Paul E. Konopka
Attorney, Agent, or Firm—Curtis, Morris & Safford

[57] ABSTRACT

Method for regenerating catalysts containing molybdenum, phosphorus, and vanadium in oxidic association and useful for the oxydehydrogenation of isobutyric acid or its lower esters to form methacrylic acid or its lower esters, by oxidizing the spent catalyst with an oxygen containing gas at temperatures from 200° C. to 400° C., suitably intermittently and in alternation with oxydehydrogenation.

3 Claims, No Drawings

OXIDATIVE CATALYST REGENERATION

The present invention relates to methods for the regeneration of catalysts which are used in the oxydehydrogenation of isobutyric acid or its esters to form methacrylic acid or its esters, which catalysts contain molybdenum, phosphorus, and vanadium as essential elements in oxidic association and are prepared from heteropolyacids of molybdenum.

THE PRIOR ART

The catalytic oxydehydrogenation of isobutyric acid or its esters to form methacrylic acid or its esters is known in the prior art. In addition to catalysts comprising iron phosphate, catalysts prepared from heteropolyacids of molybdenum, especially those which further contain phosphorus and vanadium and other optional elements, in particular metal ions, have attracted considerable attention because of their higher selectivity. Active and selective catalysts prepared from heteropolyacids of molybdenum, such as $H_5PMo_{10}V_2O_{40}$ or its metal derivatives, are described in U.S. Pat. No. 4,146,574 incorporated herein by reference and in European Patent Publications Nos. 0,079,491 and 0,113,084, for example.

These materials include phosphomolybdic acids of the formula $$H_3PMo_{12}O_{40},$$

vanadium derivatives thereof of the formula $$H_{3+x}PMo_{12-x}V_xO_{40},$$

wherein x is 1, 2, or 3, the metal salts of these acids, and combinations of the acids, the salts, and of the acids and salts as described in the copending U.S. application of Klaus Langerbeins entitled "Heteropolymolybdate catalysts and method for oxydehydrogenation."

The catalysts can thus be represented by the formula $$H_aM_bPMo_dV_eO_{40},$$

wherein M is an ion of at least one metal, preferably of Li, Na, K, Rb, Cs, Mg, Ca, Zn, Al, Ce, Ti, Zr, Sn, Sb, As, Bi, Cr, Mn, Fe, Co, Ni, or Cu, a has a value from 0 to 6, b has a value from 0 to 6, d has a value from 9 to 12, and e has a value from 0 to 3.

From a consideration of charge balance, it will be seen that, further, $a+bz=3$ and $a+bz=75-6d-5e,$ where z is the valence of metal ion M.

Catalysts wherein M is at least one of Cu, Cs, Rb, K, Ti, Ce, Mn, Fe, Bi, Cr, and As are preferred.

These catalysts are preferably used diluted with an inert carrier. Such catalysts used for the oxydehydrogenation of isobutyric acid or its lower esters do not retain the maximum activity and selectivity which they attain after being broken in for an extended period of time, as they should in commercial processes, but steadily lose effectiveness after a few days.

The loss of catalytic effectiveness is a problem that is frequently encountered in catalysts, including heterogeneous catalysts in the gas phase. In view of the many factors which influence the activity and selectivity of catalysts in a wide variety of catalytic processes, there are a great many potential and known techniques for their regeneration (See Ullmann's *Encyklopaedie der technischen Chemie,* 4th Ed., Vol. 13, p. 518 and pp. 544 et seq.) Low cost regenerations are regenerations in which the catalyst can remain in the reactor.

According to U.S. Pat. No. 4,052,333, the regeneration of a molybdenum-containing catalyst having the composition $Mo_{11.1}BiCo_{4.5}Ni_{2.5}Fe_{3.0}K_{0.41}P_{0.19}O_n$ which has been deactivated by the ammoxidation of olefins is accomplished by heating it to 550° C. and passing an air stream mixture over it for two hours. The regeneration temperature of 550° C. is considerably higher—by about 120° C.—than what is said to be the operating temperature of the catalyst in the ammoxidation of propylene.

THE OBJECT OF THE INVENTION

Thus there has been a need for effecting the regeneration of spent isobutyric acid or ester oxydehydrogenation catalysts comprising heteropolymolybdates and for developing a process for catalytic oxydehydrogenation and regeneration of the catalyst without taking the reactor containing the catalyst out of service.

It has been found that heteropolymolybdate catalysts which contain molybdenum, phosphorus, and vanadium as essential elements and which have been partly deactivated in the oxydehydrogenation of isobutyric acid or its esters are regenerated, that is have their activity and selectivity restored, when they are subjected to an oxidizing treatment using an oxygen containing gas, and especially air, at temperatures ranging from 200° C. to 400° C., and more particularly from 250° C. to 380° C.

The invention thus relates to a method for the regeneration of catalysts containing molybdenum, phosphorus, and vanadium as oxides, optionally together with further elements, in particular metals as cations, in the oxydehydrogenation of isobutyric acid or its lower esters to form methacrylic acid or its lower esters, which process is characterized in that a catalyst prepared from phosphomolybdic acid and/or its vanadium derivatives and/or their salts is regenerated by oxidizing treatment using an oxygen containing gas at temperatures ranging from 200° C. to 400° C.

It is surprising that catalysts containing molybdenum can be regenerated by being oxidized at temperatures below 400° C., which is in contact with the prior art. In fact, it has unexpectedly been found that catalysts comprising heteropolymolybdates which are used in the oxydehydrogenation of isobutyric acid or its esters, for example catalysts prepared from $H_5PMo_{10}V_2O_{40}$ or its metal salts, cannot be regenerated at temperatures above 400° C. but are deactivated even more severely at these temperature.

The invention makes it possible to carry out the regeneration of spent catalyst following oxydehydrogenation without having to adopt complicated technical measures.

It has further been found that deactivation of the catalyst during the oxydehydrogenation of isobutyric acid or isobutryic esters is considerably retarded if after an oxydehydrogenation cycle the catalyst is exposed to the regeneration conditions of the invention while in the reactor system, and that the duration of the regeneration cycle may differ from and in particular be shorter than the duration of the oxydehydrogenation cycle.

The catalytic process may thus be operated continuously or continuously/cyclically. By substantially extending the life of the catalyst and by doing away with the need for interruptions of production due to reactor downtime, the invention makes possible the manufacture of methacrylic acid or its lower esters such as methyl methacrylate by the catalytic oxydehydrogenation of isobutyric acid or its lower esters, such as methyl isobutyrate, in a more economical and technologically simpler manner than in the prior art.

PRACTICE OF THE INVENTION

The oxidative dehydrogenation of isobutyric acid or its esters to form methacrylic acid or its esters on catalysts which contain molybdenum, phosphorus, vanadium, and further optional elements, in particular metals, in oxidic association, preferably dispersed with an inert carrier, is known in the art, cf. European Patent Publication No. 0,079,491, for example. The catalyst can be used in different shapes and sizes (cf. Ullmann's *Encyklopaedie der technischen Chemie*, 4th Ed., Vol. 13, pp. 558–565 re catalyst forming) and the reaction is carried out at temperatures ranging from 250° C. to about 400° C. in the presence of gases containing oxygen, such as air, optionally with additions of other inert gases such as nitrogen, steam, carbon dioxide, or recycling gas from the isolation of the reaction product. The starting mixture contains about 1 to 4 moles of oxygen, normally as an addition to air, per mole of isobutyric acid or its esters. The selectivity for the desired reaction product is determined mainly by the molar ratio between oxygen and isobutyric acid or ester. The amount of reaction product generally decreases as the amount of oxygen increases, and by-products, especially carbon dioxide and carbon monoxide, increase markedly. In embodiments where methacrylic acid or its esters are the desired end products, the catalyst is then exposed practically all the time to reducing conditions, with the catalyst matrix continually undergoing further deactivation of active sites. Under these operating conditions, catalytically essential elements which are present in lower valence states are reoxidized less and less frequently so that the potential of the catalyst continually drops.

It is therefore necessary to remove spent catalyst from reducing conditions from time to time and to expose it to catalytically regenerative oxidizing conditions. In accordance with the invention, regeneration is accomplished by subjecting spent oxidation catalyst to an oxidizing treatment with an oxygen containing gas at temperatures from 200° C. to 400° C. The oxidative regenerating gas is preferably free of oxidizable carbon compounds. However, it may contain minor amount of such compounds, in which case the amount of oxygen contained in the oxidative regenerating gas should be greater than the amount of oxygen required for complete combustion of any carbon compounds which it may contain. The regenerated catalyst is then reused catalytically.

The oxygen content of the regenerating gas ranges from 5 to 40 volume percent, and preferably from 10 to 21 volume percent. Like the oxydehydrogenation, the regeneration is carried out at pressures ranging from about 0.1 to about 5 bar, and more particularly from 0.5 to 2.5 bar. This can be done by various operating techniques. Regeneration of the catalyst in a fixed bed reactor, for example, is carried out at intervals by exposing the catalyst to a stream of oxidizing gas, for example air, for a certain length of time in the reactor, practically under the temperature conditions of the oxydehydrogenation, after the feed of reactant to the oxydehydrogenation has been shut off. The desired temperature between 200° C. and 400° C. can be established by shutting off the reactant feed in such a way that high combustion rates, and hence overheating of the catalyst, are prevented since these would entail destruction of the catalyst structure, and optionally by appropriate preheating of the oxygen containing regenerating gas, which may also contain steam. The stream of oxidizing gas may be diluted with further inert gases, particularly at the start of regeneration. The process may be operated so that the oxydehydrogenation cycles range from a few minutes to several hours and the regeneration time should be limited to just a few minutes, if possible. This permits the oxydehydrogenation to be carried out, in a fixed bed reactor for example, in an intermittent yet practically continuous manner. In this way, fully continuous operation with constant space-time yields is obtained over the entire life of the catalyst.

A better understanding of the present invention and of its many advantages will be had by referring to the following specific Examples, given by way to illustration.

EXAMPLES

Example 1

A vaporous mixture of isobutyric acid and air in a molar ratio of isobutyric acid to oxygen of 1:1.5 and at a pressure of 1 atmosphere (20° C.) is reacted at 320° C. and with a dwell time of 0.6 second in a circulating reactor known in the art (cf. published German Patent Application DOS No. 30 19 731) on a catalyst composed of 70 percent by weight of $H_5PMo_{10}V_2O_{40}$, 25 percent by weight of diatomaceous earth, and 5 percent by weight of finely divided silica gel, the last two mentioned components comprising an inert carrier. The catalyst loading is 2.5 kg isobutyric acid per kg of catalytic mass per hour.

Regeneration of the catalyst according to the present invention is carried out after 75, 100, 150 and 200 hours. The regeneration cycle in the air stream (with the isobutyric acid feed shut off) has a duration of 1 hour and is carried out at 350° C.

The conversion and selecting of such a catalyst is shown in following Table I as a function of time.

TABLE I

| Operating time (hr.) | Isobutyric acid conversion (%) | Selectivity for methacrylic acid (%) | Regeneration |
|---|---|---|---|
| 1 | 51 | 71 | |
| 30 | 47 | 71 | |
| 75 | 43 | 69 | |
| 76 | — | — | 1 hr. at 350° C. |
| 80 | 50 | 70 | |
| 100 | 46 | 66 | |
| 101 | — | — | 1 hr. at 350° C. |
| 105 | 50 | 68 | |
| 130 | 45 | 66 | |
| 150 | 43 | 64 | |
| 151 | — | — | 1 hr. at 350° C. |
| 155 | 49 | 68 | |
| 180 | 47 | 66 | |
| 200 | 44 | 64 | |
| 201 | — | — | 1 hr. at 350° C. |
| 205 | 49 | 67 | |
| 240 | 45 | 63 | |

Comparative Example 1

The same $H_5PMo_{10}V_2O_{40}$ catalyst used under the same oxydehydrogenation conditions as in Example 1 but not regenerated in accordance with the invention shows a much steeper decline in conversion and selectivity (cf. Table II).

TABLE II

| Operating time (hr.) | Isobutyric acid conversion (%) | Selectivity for methacrylic acid (%) |
|---|---|---|
| 1 | 51 | 68 |
| 150 | 30 | 64 |
| 250 | 22 | 53 |
| 300 | 21 | 50 |

Example 2

A vaporous mixture of isobutyric acid and oxygen (as air) in a molar ratio of 1:1.5 at a pressure of 1 atmosphere (measured at 20° C.) is reacted over a $H_5PMo_{10}V_2O_{40}$ catalyst as described in Example 1 at 320° C. and with a dwell time of 0.6 sec. The catalyst loading is 2.5 kg isobutyric acid per kg of catalytic mass per hour.

During the first 210 hours, the catalyst is regenerated every 2 hours for 5 minutes and thereafter every 27 minutes for 3 minutes by cutting off the isobutyric acid. The temperature is maintained at 320° C. during the regeneration.

The characteristics of the catalyst are shown in following Table III.

TABLE III

| Operating time (hr.) | Isobutyric acid conversion (%) | Selectivity for methacrylic acid (%) | Regeneration |
|---|---|---|---|
| 1 | 51 | 71 | Every 2 hours for 5 minutes |
| 20 | 51 | 71 | |
| 60 | 50 | 70 | |
| 120 | 47 | 69 | |
| 180 | 46 | 69 | |
| 210 | 45 | 68 | |
| 220 | 45 | 68 | Every 27 min. for 3 minutes |
| 260 | 45 | 68 | |
| 330 | 44 | 67 | |

Example 3

A vaporous mixture of isobutyric acid, $O_2$ (as air), and $H_2O$ in a molar ratio of 1:1.5 at a pressure of 1 atmosphere (at 20° C.) is reacted over a catalyst containing 70 percent by weight of $Cu_{0.2}H_{3.6}PMo_{11}V_1O_{40}$ and 30 percent by weight of carrier comprising diatomaceous earth and silica gel in a weight ratio of 5:1 in a circulating reactor at 320° C. and with a dwell time of 0.6 sec. The catalyst loading is 2.5 kg isobutyric acid per kg of catalytic mass per hour. The 3 minutes regeneration is carried out every 27 minutes in an air stream at 320° C. by cutting off the isobutyric acid.

The results are shown in Table IV.

TABLE IV

| Operating time (hr.) | Isobutyric acid conversion (%) | Selectivity for methacrylic acid (%) | Regeneration |
|---|---|---|---|
| 1 | 60 | 75 | Every 27 min. for 3 minutes |
| 60 | 60 | 75 | |
| 120 | 59 | 75 | |
| 180 | 57 | 75 | |
| 240 | 56 | 75 | |
| 300 | 55 | 74 | |

Comparative Example 3

A $Cu_{0.2}H_{3.6}PMo_{11}V_1O_{40}$ catalyst used under the same oxydehydrogenation conditions as in Example 3 but without regeneration and without $H_2O$ addition shows a much steeper decline in conversion and selectivity, as is evident from Table V.

TABLE V

| Operating time (hr.) | Isobutyric acid conversion (%) | Selectivity for methacrylic acid (%) |
|---|---|---|
| 1 | 50 | 72 |
| 60 | 44 | 71 |
| 120 | 33 | 70 |
| 180 | 25 | 66 |
| 240 | 21 | 61 |
| 300 | 19 | 55 |

TABLE VI

| | Catalyst | Conversion (C) and Selectivity (S) | | | | | | | | Regeneration Condition | |
|---|---|---|---|---|---|---|---|---|---|---|---|
| | | $C_0$ (%) | $S_0$ (%) | $C_1$ (%) | $S_1$ (%) | $C_2$ (%) | $S_2$ (%) | T (°C.) | t (min.) | $O_2:N_2$ volume ratio in oxygenating gas | P (atm) |
| Ex. 4 | $Cr_{0.2}H_{3.3}PMo_{10.5}V_{1.5}O_{40}$ | 74.3 | 71.0 | 69.2 (70 h) | 71.0 | 74.0 | 71.0 | 300 | 30 | 15:85 | 1 |
| Ex. 5 | $Mn_{0.2}H_{4.1}PMo_{10.5}V_{1.5}O_{40}$ | 82.8 | 71.4 | 74.9 (80 h) | 71.4 | 83.0 | 71.0 | 360 | 15 | 21:79 | 1.5 |
| Ex. 6 | $Cu_{0.2}Ti_{0.01}Fe_{0.01}Bi_{0.01}H_{3.5}PMo_{11}V_1O_{40}$ | 86.5 | 75.6 | 79.1 (120 h) | 75.0 | 86.7 | 75.0 | 340 | 15 | 21:79 | 1 |
| Ex. 7 | $Cu_{0.05}H_{4.9}PMo_{10}V_2O_{40}$ | 80.2 | 72.5 | 72.8 (70 h) | 73.3 | 79.8 | 73.0 | 320 | 20 | 30:70 | 2 |
| Ex. 8 | $K_{0.1}H_{4.9}PMo_{10}V_2O_{40}$ | 79.0 | 73.1 | 74.4 (80 h) | 73.4 | 79.5 | 72.5 | 340 | 20 | 21:79 | 0.5 |
| Ex. 9 | $Ce_{0.4}H_{2.9}PMo_{10.5}V_{1.5}O_{40}$ | 84.7 | 72.0 | 81.2 (95 h) | 71.6 | 83.8 | 71.0 | 340 | 20 | 21:79 | 1 |
| Ex. 10 | $Cs_{0.2}H_{4.3}PMo_{10.5}V_{1.5}O_{40}$ | 81.7 | 72.4 | 77.8 (120 h) | 72.0 | 81.0 | 71.7 | 340 | 20 | 21:79 | 1 |

$C_0$, $S_0$ = values at the beginning of the oxydehydrogenation
$C_1$, $S_1$ = values at the time indicated, but before regeneration
$C_2$, $S_2$ = values after regeneration

Examples 4-10

(A) Preparation of the Catalysts

To prepare the heteropolyacid catalysts of Examples 4, 5, 9, and 10, equimolar amounts of the known heteropolyacids $H_5PMo_{10}V_2O_{40}$ and $H_4PMo_{11}VO_{40}$ and the amount of metal additive required by the formula are mixed together in an aqueous medium, optionally with heating, and then diluted with diatomaceous earth and silica gel to give the catalyst. Cr is added as $CrO_3$, Mn as $Mn(CO_3)_2$, Ce as $Ce(NO_3)_4$, and Cs as $Cs_2CO_3$.

To prepare the catalysts of Examples 6, 7, and 8, the heteropolyacids $H_4PMo_{11}VO_{40}$ or $H_5PMo_{10}V_2O_{40}$ are mixed together in an aqueous medium with the amount of metal required by the formula and then diluted with diatomaceous earth and silica gel to give the catalyst.

Cu is added as CuO, Ti as $Ti(O-i-propyl)_4$, Fe and Bi as their nitrates in nitric acid solution, and K as KOH.

(B) Oxydehydrogenation with Regeneration

A vaporous mixture of isobutyric acid, $O_2$ (from air), and $N_2$ in a molar ratio of 1:1.5:7.71 and at a pressure of 1 atmosphere (measured at 20° C.) is brought to reaction at 340° C. and a dwell time of 1 second over the heteropolyacid catalyst indicated in following Table VI after dilution of the active catalyst ingredients with a mixture of diatomaceous earth and finely divided silica gel, (5:1) to give a catalyst containing 70 percent by weight of the active ingredients and 30 percent by weight of the diluent. The loading of the catalyst in this fashion amounts to 1.25 kg of isobutyric acid per kg of catalytic mass per hour.

The regeneration conditions (pressure, temperature, time, gas composition) are given in Table VI. Regeneration is effected by cutting off the isobutyric acid. The gas volume is 800 liters per kg of catalyst mass per hour, measured at 20° C.

The results of the oxydehydrogenation with intervening regeneration are reported in Table VI.

We claim:

1. A method for regenerating a solid catalyst used in oxydehydrogenation of isobutyric acid or its lower esters to form methacrylic acid or its lower esters, having the formula $$H_aM_bPMo_dV_eO_{40}$$

wherein
M is at least one metal ion,
a has a value from 0 to 6,
b has a value from 0 to 6,
d has a value from 9 to 12
e has a value from 0 to 3,
a+bz has a value equal to or greater than 3, and
a+bz is equal to 75−6d−5e, where z is the valence of metal ion M, which method comprises contacting said solid catalyst at a temperature from 200° C. to 400° C. with a gas containing from 5 to 40 volume percent of elemental oxygen, said gas having a pressure from 0.1 bar to about 5 bar.

2. A method as in claim 1 wherein said gas contains from 10 to 21 volume percent of oxygen.

3. A method as in claim 1 carried out intermittently to alternate with oxydehydrogenation cycles in a fixed bed reactor.

* * * * *